US00PP24767P2

(12) United States Plant Patent
van der Sar

(10) Patent No.: US PP24,767 P2
(45) Date of Patent: Aug. 12, 2014

(54) ***COREOPSIS* PLANT NAMED 'SYLVESTER'**

(50) Latin Name: *Coreopsis verticillata*
Varietal Denomination: Sylvester

(75) Inventor: Maarten van der Sar, Maasland (NL)

(73) Assignee: Takii Europe B.V., De Kwakel (NL)

( * ) Notice: Subject to any disclaimer, the term of this patent is extended or adjusted under 35 U.S.C. 154(b) by 187 days.

(21) Appl. No.: 13/573,082

(22) Filed: Aug. 20, 2012

(51) Int. Cl.
*A01H 5/00* (2006.01)

(52) U.S. Cl.
USPC ..... Plt./417

(58) Field of Classification Search
CPC ..... A01H 5/025; A01H 5/02
USPC ..... Plt./417
See application file for complete search history.

*Primary Examiner* — June Hwu
(74) *Attorney, Agent, or Firm* — Audrey Charles

(57) ABSTRACT

A new and distinct cultivar of *Coreopsis* plant named 'Sylvester', characterized by its bright yellow-colored inflorescences, medium green-colored, deeply-dissected foliage having thread-like segments, moderate growth vigor, well-branched, upright-mounded, compact growth habit, is disclosed.

1 Drawing Sheet

Latin name of genus and species of plant claimed: *Coreopsis verticillata.*

Variety denomination: 'Sylvester'.

BACKGROUND OF THE INVENTION

The present invention relates to a new and distinct cultivar of *Coreopsis* plant botanically known as *Coreopsis verticillata* and hereinafter referred to by the cultivar name 'Sylvester'.

The new cultivar originated from an open pollination in June 2003 in a controlled nursery location in Boskoop, The Netherlands. The female (seed) parent of the new cultivar is 'Zagreb', not patented, characterized by its bright yellow-colored inflorescences, medium green-colored, deeply-dissected foliage having thread-like segments, and upright-mounded, compact growth habit. The male (pollen) parent of the new cultivar is unknown. The new cultivar was discovered and selected as a single flowering plant within the progeny of the above stated open-pollination during June 2007 in a controlled environment in Boskoop, The Netherlands.

Asexual reproduction of the new cultivar by terminal stem cuttings since June 2007 in Boskoop, The Netherlands has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Sylvester' as a new and distinct cultivar of *Coreopsis* plant:

1. Bright yellow-colored inflorescences;
2. Medium green-colored, deeply-dissected foliage having thread-like segments;
3. Moderate growth vigor;
4. Well-branched, upright-mounded, compact growth habit.

Of the many commercially available *Coreopsis* cultivars, the most similar in comparison to the new cultivar is the female parent 'Zagreb', not patented. However, in side by side comparisons, plants of the new cultivar differ from plants of 'Zagreb' in at least the following characteristics:

1. Plants of the new cultivar are shorter than plants of 'Zagreb';
2. Plants of the new cultivar have smaller diameter flowers than plants of 'Zagreb'; and
3. Plants of the new cultivar are better branched than plants of 'Zagreb'.

In addition plants of the new cultivar are similar to the *Coreopsis* cultivar 'Tweety', U.S. Plant Pat. No. 23,347. However, in side by side comparisons, plants of the new cultivar differ from plants of 'Tweety' in at least the following characteristics:

1. Plants of the new cultivar have a darker foliage color than plants of 'Tweety';
2. Plants of the new cultivar are wider than plants of 'Tweety'; and
3. Plants of the new cultivar have a larger diameter inflorescence than plants of 'Tweety'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Sylvester'. One plant per 1 gallon container was grown for approximately 16 weeks in a greenhouse in Elburn, Ill.

DETAILED BOTANICAL DESCRIPTION

Figure 1:
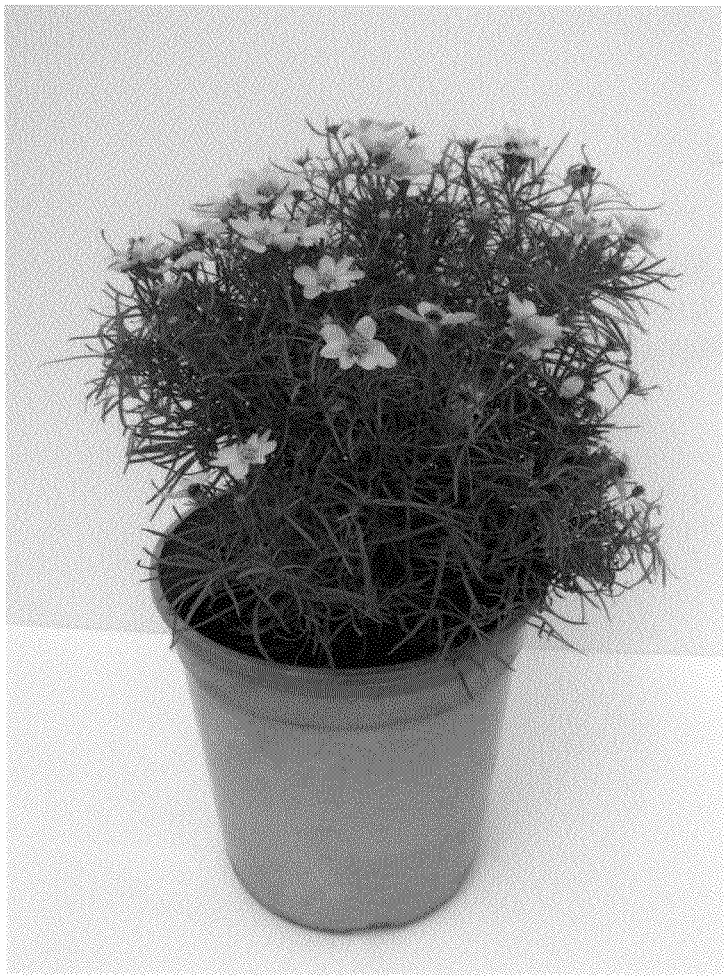
FIG. 1 illustrates a side view of the overall growth and flowering habit of 'Sylvester'.
Figure 2:
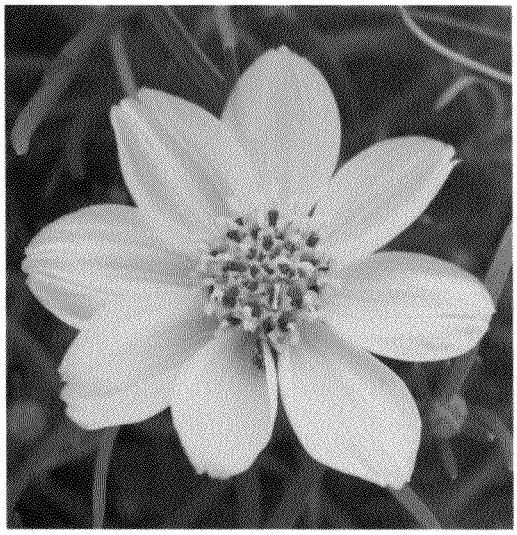
FIG. 2 illustrates a close-up view of an inflorescence of 'Sylvester'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in July 2012 under natural light conditions in West Chicago, Ill.

The following descriptions and measurements describe plants produced from in vitro plantlets and grown in a glass-covered greenhouse under conditions comparable to those used in commercial practice. The plants were grown in Elburn, Ill. in 1-gallon pots for approximately 16 weeks utilizing a soilless growth medium. Greenhouse temperatures were maintained at approximately 50° F. to 70° F. (10.0° C. to 21.1° C.) during the day and approximately 35° F. to 50° F. (1.7° C. to 10.0° C.) during the night. No supplemental lighting was provided. Measurements and numerical values represent averages of typical plants.

Botanical classification: *Coreopsis verticillata* cultivar Sylvester.

Parentage:

*Female parent*.—'Zagreb', not patented.

*Male parent*.—Unknown *Coreopsis verticillata* plant.

Propagation:

*Type cutting*.—Terminal stem.

*Time to initiate roots*.—Approximately 21 days at 20° C.

*Time to produce a rooted cutting*.—Approximately 42 days at 20° C.

*Root description*.—Fibrous, thin, white in color.

*Rooting habit*.—Freely branching, dense.

Plant description:

*Commercial crop time*.—Approximately 10 to 12 weeks from a rooted cutting to finish in a one-gallon container.

*Growth habit and general appearance*.—Herbaceous perennial, moderate growth vigor, well-branched, upright-mounded, compact growth habit.

*Size*.—Height from soil level to top of plant plane: Approximately 20.5 cm. Width: Approximately 26.0 cm.

*Branching habit*.—Freely branching, pinching improves basal branching. Quantity of lateral branches per plant: Approximately 45.

*Lateral branch*.—Strength: Strong. Length: Approximately 7.5 cm. Diameter: Approximately 2.0 mm. Length of central internode: Approximately 1.7 cm. Texture: Slightly glossy, glabrous. Color of young and mature stems: 144A.

Foliage description:

*General description*.—Quantity of leaves per lateral branch: Approximately 12. Fragrance: None detected. Form: Single. Arrangement: Opposite.

*Leaves*.—Aspect: Acute angle to stem; perpendicular to obtuse angle to stem with age. Shape: Upper leaves linear, lower mature leaves overall shape ovate having three to five linear lobes having a thread-like appearance. Margin: Entire, deeply dissected. Apex of divisions: Acuminate. Base: Sessile, truncate. Venation pattern: Pinnate. Length of mature leaf: Approximately 3.6 cm. Width of mature leaf: 3.1 cm. Texture of upper surface: Very slightly glossy, glabrous. Texture of lower surface: Moderately glossy, glabrous. Color of upper and lower surfaces of young foliage: 143B with indistinguishable venation. Color of upper and lower surfaces of mature foliage: 137B indistinguishable venation.

Flowering description:

*Flowering habit*.—'Sylvester' is freely flowering under outdoor growing conditions with substantially continuous blooming from spring through autumn and year-round in greenhouse environment.

*Lastingness of individual inflorescence on the plant*.—Approximately 14 days.

Inflorescence description:

*General description*.—Type: Daisy-type composite, actinomorphic. Persistent. Shape: Round. Aspect: Erect. Arrangement: Terminal capitulum, positioned above and below the foliage. Quantity per plant: Approximately 22. Diameter: Approximately 3.0 cm. Depth: Approximately 8.0 mm. Fragrance: None detected.

*Peduncle*.—Strength: Strong. Aspect: Erect. Length: Approximately 2.5 cm. Diameter: Less than 1.0 mm. Texture: Glabrous, slightly glossy. Color: Closest to 137B.

*Bud*.—Rate of opening: Generally takes 4 to 5 days for bud to progress from first color to fully open inflorescence. Quantity per plant: Approximately 50.

*Bud just before opening*.—Shape: Oblate. Diameter: Approximately 4.0 mm. Depth: Approximately 3.0 mm. Color: 152A to 152B.

*Ray florets*.—Quantity per inflorescence: Approximately 8. Arrangement: In a single whorl, slightly imbricate. Aspect: Slightly concave. Shape: Elliptic. Margin: Entire. Apex: Three acute tips. Base: Cuneate. Length: Approximately 1.3 cm. Width: Approximately 7.0 mm. Texture of upper and lower surfaces: Glabrous, axially ribbed. Color of upper and lower surfaces when first open: 13A. Color of upper and lower surfaces when fully open: 12A.

*Disc florets*.—Quantity per inflorescence: Approximately 28. Arrangement: Massed in center of inflorescence. Shape: Tubular, lower 90% fused. Margin: Entire. Apex: Five acute tips. Base: Fused. Length: Approximately 8.0 mm. Diameter: Approximately 2.0 mm. Texture of outer surface: Slightly glossy, glabrous. Texture of inner surface: Glandular pubescent on tips. Color of upper or inner surface when first and fully open: 151D with tips of 1A. Color of lower or outer surface when fully open: 151D with tips of 1A.

*Disc*.—Diameter: Approximately 1.0 cm. Depth: Approximately 5.0 mm.

*Receptacle*.—Shape: Cone. Height: Approximately 1.0 mm. Diameter at base: Approximately 3.0 mm. Color: 144B to 144C.

*Phyllaries*.—Quantity per inflorescence Approximately 16. Arrangement: In two equally divided whorls. Base of outer bracts fused into cup-shaped base, inner bracts surround receptacle, slightly imbricate, held close to ray florets.

*Outer phyllaries*.—Shape of free portion: Lanceolate. Margin: Entire. Apex: Acute. Base: Fused. Length: Approximately 5.0 mm. Width: Approximately 1.0 mm. Texture of upper and lower surfaces: Glabrous, glossy. Color of upper and lower surfaces: N137B.

*Inner phyllaries*.—Shape: Ovate. Margin: Entire. Apex: Broadly acute. Base: Truncate. Length: Approximately 4.0 mm. Width: Approximately 2.5 mm. Texture of upper and lower surfaces: Glabrous, slightly glossy. Color of upper and lower surfaces: 152C to 152D.

*Reproductive organs*.—Androecium: Present on disc florets only. Stamen quantity: 5. Stamen length: Approximately 4.0 mm. Filament length: Approximately 2.0 mm. Filament color: 150C. Anther shape: Oblong, basifixed. Anther length: Approximately 2.0 mm. Anther color: 200A. Pollen amount: Moderate to abundant. Pollen color: 12A. Gynoecium: Present on ray and disc florets. Pistil quantity: 1 per floret. Pistil length: Approximately 8.0 mm. Stigma shape: Cleft. Stigma length: Approximately 1.0 mm. Stigma color: 154C. Style length: Approximately 5.0 mm. Style color: 154C to 154D. Ovary length: Approximately 2.0 mm. Ovary color: 151D.

Seed and fruit production: Neither seed nor fruit production has been observed.

Disease and pest resistance: Resistance to pathogens and pests common to *Coreopsis* has not been observed.

What is claimed is:

1. A new and distinct cultivar of *Coreopsis* plant named 'Sylvester', substantially as herein shown and described.

* * * * *